United States Patent
Tee et al.

(10) Patent No.: US 9,125,788 B2
(45) Date of Patent: Sep. 8, 2015

(54) SYSTEM AND METHOD FOR MOTOR LEARNING

(75) Inventors: Keng Peng Tee, Singapore (SG); Cuntai Guan, Singapore (SG); Haihong Zhang, Singapore (SG); Brahim Ahmed Salah Hamadi Charef, Singapore (SG)

(73) Assignee: AGENCY FOR SCIENCE TECHNOLOGY AND RESEARCH, Singapore (SG)

( * ) Notice: Subject to any disclaimer, the term of this patent is extended or adjusted under 35 U.S.C. 154(b) by 883 days.

(21) Appl. No.: 13/376,097

(22) PCT Filed: Jun. 2, 2009

(86) PCT No.: PCT/SG2009/000193
§ 371 (c)(1),
(2), (4) Date: Feb. 27, 2012

(87) PCT Pub. No.: WO2010/140975
PCT Pub. Date: Dec. 9, 2010

(65) Prior Publication Data
US 2012/0143104 A1    Jun. 7, 2012

(51) Int. Cl.
*A61B 5/04* (2006.01)
*A61H 1/02* (2006.01)
*A61B 5/0488* (2006.01)
*A61B 5/1455* (2006.01)

(52) U.S. Cl.
CPC ............... *A61H 1/02* (2013.01); *A61B 5/04001* (2013.01); *A61B 5/04008* (2013.01); *A61B 5/0488* (2013.01); *A61B 5/14553* (2013.01); *A61H 2201/501* (2013.01); *A61H 2201/5061* (2013.01); *A61H 2201/5069* (2013.01); *A61H 2230/08* (2013.01); *A61H 2230/10* (2013.01); *A61H 2230/60* (2013.01)

(58) Field of Classification Search
CPC ............... A61B 5/0476; A61B 5/0482; A61H 2201/1215; A61H 2201/5007
USPC .................................. 600/544, 545; 601/5, 33
See application file for complete search history.

(56) References Cited

U.S. PATENT DOCUMENTS

| | | |
|---|---|---|
| 5,466,213 A | 11/1995 | Hogan et al. |
| 2006/0167371 A1* | 7/2006 | Flaherty et al. ............... 600/545 |
| 2006/0211956 A1 | 9/2006 | Sankai |

FOREIGN PATENT DOCUMENTS

| | | |
|---|---|---|
| JP | 2004254876 | 9/2004 |
| WO | 2005087307 A2 | 9/2005 |

OTHER PUBLICATIONS

Parry et al. "Effect of severity of arm impairment on response to additional physiotherapy early after stroke," Clinical Rehabilitation, vol. 13, pp. 187-198 (1999).

Kwakkel et al. "Effects of intensity of rehabilitation after stroke. A research synthesis," Stroke, vol. 28, pp. 1550-1556 (Aug. 1997).

(Continued)

*Primary Examiner* — Etsub Berhanu
(74) *Attorney, Agent, or Firm* — Conley Rose, P.C.

(57) ABSTRACT

A method and system for motor learning. The method comprises the steps of detecting a user's motor intent; and giving robotic assistance to the user for executing a motor task associated with the motor intent based on the detected motor intent.

18 Claims, 5 Drawing Sheets

(56) References Cited

OTHER PUBLICATIONS

Nef et al. "ARMin—Design of a Novel Arm Rehabilitation Robot," Member, IEEE, 9th International Conference on Rehabilitation Robotics, pp. 57-60 (Jun. 28-Jul. 1, 2005).

Krebs et al. "Robot-aided neurorehabilitation.," IEEE Transactions on Rehabilitation Engineering, vol. 6, No. 1, pp. 75-87 (Mar. 1998).

Volpe et al. "A novel approach to stroke rehabilitation: Robot-aided sensorimotor stimulation," Neurology, 54(10): 1938-1944 (May 23, 2000).

Riener et al. "Human-Centered Rehabilitation Robotics," in Proc 9th International Conference on Rehabilitation Robotics (ICORR 2005), pp. 319-322 (Jul. 2005).

Fasoli et al. "Effects of Robotic Therapy on Motor Impairment and Recovery in Chronic Stroke", Arch Phys Med Rehabil vol. 84, pp. 477-482 (Apr. 2003).

Buerger et al. "Rehabilitation Robotics: Adapting Robot Behavior to Suit Patient Needs and Abilities", Boston, Massachusetts, pp. 3239-3244 (Jun. 30-Jul. 2, 2004).

Krebs et al. "Rehabilitation Robotics: Performance-Based Progressive Robot-Assisted Therapy", Autonomous Robots 15, 7-20, pp. 8-20 (2003).

Tee et al. "Augmenting Cognitive Processes in Robot-Assisted Motor Rehabilitation", Institute for Infocomm Research, Scottsdale, AZ, USA, pp. 698-703 (Oct. 19-22, 2008).

Neville Hogan, "Impedance Control: An Approach to Manipulation", Transactions of the ASME, vol. 107, pp. 8-16 (Mar. 1985).

Ang et al. "Filter Bank Common Spatial Pattern (FBCSP) in Brain-Computer Interface", International Joint Conference on Neural Networks, pp. 2390-2397 (Oct. 22, 2008).

Lum et al. "Evidence for Improved Muscle Activation Patters After Retraining of Reaching Movements with the Mime Robotic System in Subjects with Post-Stroke Hemiparesis", IEEE Transactions on Neural Systems and Rehabilitation Engineering, vol. 12, No. 2, pp. 186-194 (Jun. 2004).

Plautz et al. "Effects of Repetitive Motor Training on Movement Representations in Adult Squirrel Monkeys: Role of Use versus Learning", Neurobiology of Learning and Memory 74, pp. 27-55 (2000).

Ferraro et al. "Robot-aided sensorimotor arm training improves outcome in patients with chronic stroke", Neurology, vol. 61; pp. 1604-1607 (Apr. 11, 2003).

\* cited by examiner

SYSTEM AND METHOD FOR MOTOR LEARNING

FIELD OF INVENTION

The invention broadly relates to a system and method for motor learning.

BACKGROUND

Traditional physical and occupational therapy for stroke patients, such as the Bobath approach and the Motor Relearning Program, typically involve exercises that attempt to overcome motor deficits and improve motor patterns with the help of therapists. More recently, promising results have been demonstrated in Constraint-induced Movement Therapy, which forces the use of the affected limb by restraining the unaffected limb. Although the above rehabilitation methods are well-established in practice, they are labor intensive and expensive. Furthermore, manually assisted movement training lacks repeatability and objective measures of patient performance and therapy progress.

With the advent of robotic technology and new insights in the neuroscience of human motor adaptation, there is a paradigm shift to robot-assisted motor rehabilitation. Rehabilitation programs that incorporate robotic and information technology can ameliorate the increasing burden on manpower by automating parts of the process that are repetitive and time-consuming. Additionally, robots are able to provide pervasive and accurate monitoring of the progress of patients. However, most of the current robotic rehabilitation approaches are centered on physical therapy, and devote minimal emphasis to cognitive factors that play a role in determining rehabilitation progress and outcome.

Current approaches of robot-assisted motor rehabilitation tailor adaptive therapy only to changes in behavioral measures of motor skills and may not capture all the facets of an optimal therapy. The behavioral measures of motor performance may not provide any indication of the degree of cognitive effort or the level of psychological stress in the patient. Furthermore, the perception of task difficulty and self-evaluation of progress can vary across patients in view of individual factors that include attitude, self-motivation, and personality.

A need therefore exists to provide a system and method for motor learning that seeks to address at least one of the above-mentioned problems.

SUMMARY

According to a first aspect of the present invention there is provided a method of motor learning comprising the steps of detecting a user's motor intent; and giving robotic assistance to the user for executing a motor task associated with the motor intent based on the detected motor intent.

The method may further comprise processing signals detected by the detector to derive a score associated with the detected motor intent, and giving the robotic assistance based on the score.

The method may further comprise adjusting a threshold for giving the robotic assistance to the user for executing a motor task associated with the motor intent based on the detected motor intent.

Adjusting the robotic assistance may comprise comparing a target performance in relation to the motor task with an actual performance, and lowering the threshold for giving the robotic assistance if there is a deficit of the actual performance compared to the target performance, and increasing the threshold for giving the robotic assistance if there is a surplus in the actual performance compared to the target performance.

The target performance and the actual performance may be compared over a session, k, of $N_k$ trials, and the threshold is adjusted for a next session, k+1, based on the session k.

The method may further comprise obtaining a default threshold, $R_0$, for a first session, k=1, from a calibration process.

The detecting of the user's motor intent may be performed asynchronously.

The detecting of the user's motor intent may be performed substantially continuously.

According to a second aspect of the present invention there is provided a system for motor learning comprising a detector unit for detecting a user's motor intent; and a robotic device for giving robotic assistance to the user for executing a motor task associated with the motor intent; wherein the robotic device is configured for giving of the robotic assistance based on the detected motor intent.

The system may further comprise a processing unit for processing signals detected by the detector to derive a score associated with the detected motor intent, and the robotic device is configured for giving the robotic assistance based on the score.

The processing unit may be configured for adjusting a threshold for giving the robotic assistance to the user for executing a motor task associated with the motor intent based on the detected motor intent.

The processing unit may be configured for lowering the threshold for giving the robotic assistance if there is a deficit of an actual performance compared to a target performance, and for increasing the threshold for giving the robotic assistance if there is a surplus in the actual performance compared to the target performance.

The target performance and the actual performance may be compared over a session, k, of $N_k$ trials, and the threshold is adjusted for a next session, k+1, based on the session k.

The system may further comprise obtaining a default threshold, $R_0$, for a first session, k=1, from a calibration process.

The detector may be configured for detecting of the user's motor intent asynchronously.

The detector may be configured for detecting of the user's motor intent substantially continuously.

BRIEF DESCRIPTION OF THE DRAWINGS

Example embodiments of the invention will be better understood and readily apparent to one of ordinary skill in the art from the following written description, by way of example only, and in conjunction with the drawings, in which.

DETAILED DESCRIPTION

Figure 1:
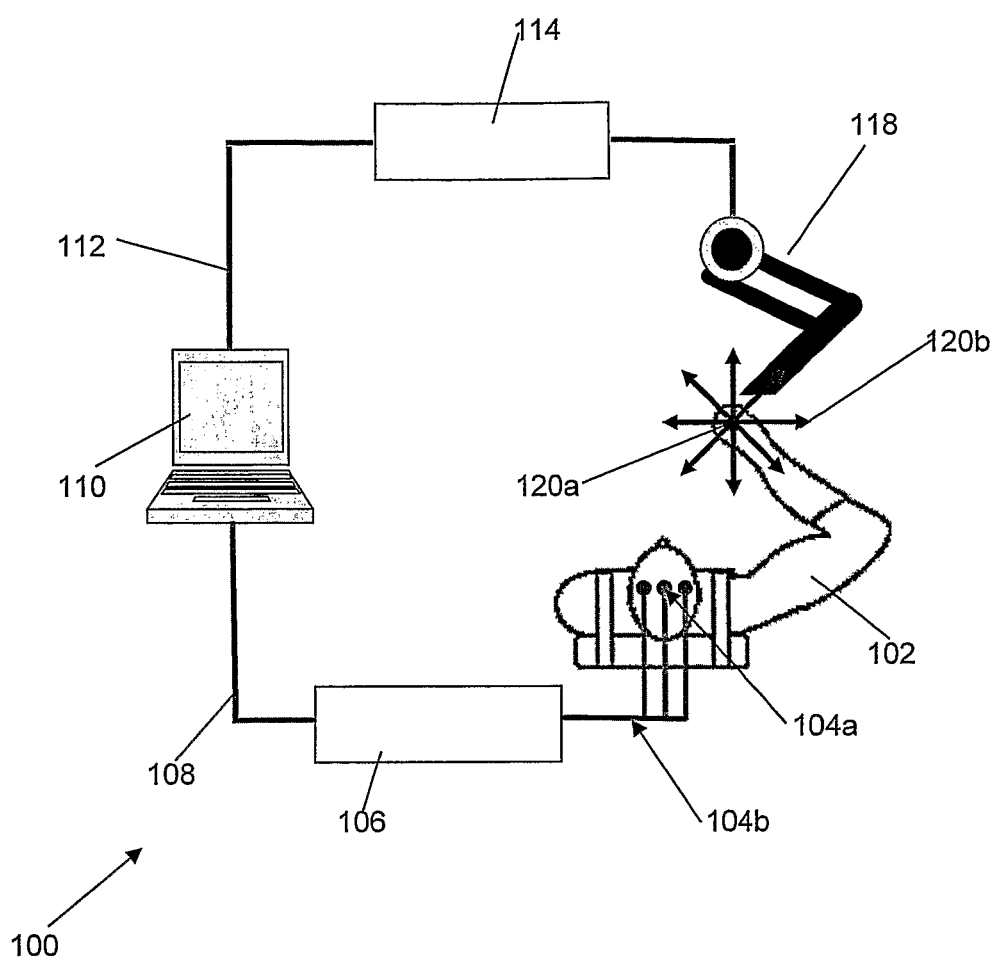
FIG. 1 is a schematic drawing illustrating a system for motor learning with an adaptive brain-robot interface, according to an example embodiment of the present invention.

Example embodiments of the present invention advantageously provide a system and method for motor learning that can lead to improved motor recovery. Example embodiments of the present invention not only consider motor output but advantageously also consider the interactions with motor intention, sensory feedback, and attention.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

FIG. 1 is a schematic drawing, designated generally as reference numeral 100, illustrating a system for motor learning with an adaptive brain-robot interface according to an example embodiment of the present invention, comprising a neural signal acquisition device 106, a computer system 110, a robot control module 114 and a robotic device 118.

The neural signal acquisition device 106 preferentially acquires and conditions, via non-invasive means, neural signals from a user 102. The non-invasive means of acquiring neural signals may include electroencephalogram (EEG), electrooculogram (EOG), electromyogram (EMG), magnetoencephalogram (MEG), near-infrared spectrogram (NIRS), or any combination of the above. There may be different sensor montages for different methods of neural signal acquisition. A plurality of electrodes 104a are attached to the scalp of the user 102. Lead wires 104b connected the electrodes 104a to the neural signal acquisition device 106.

A cable 108 connects the neural signal acquisition device 106 to the computer system 110. It will be appreciated that in different embodiment, a wireless connection may be used. The computer system 110 is preferably configured for asynchronous detection of movement intent derived from neural signals received from the neural signal acquisition device 106 and processing the neural signals; controlling the robotic device 118 via the robot control module 114; and presenting stimuli and feedback to the user 102. This configuration advantageously facilitates autonomous optimization of the level of assistance provided by the robotic device 118 to the user 102. The computer system 110 will be further described in more detail below.

The computer system 110 receives a multi-channel neural signal X(t) from the neural signal acquisition device 106 and is preferably passed through a filter to be decomposed into N sub-band signals $X_i$ (t):

$$X_i(t) = h(X(t), A_i, B_i), i=1, K, N$$

where h is a filter operator, N is an arbitrary variable that depends on the application and $A_i, B_i$ are coefficients of the filter. The filter may be designed by Infinite Impulse Response (IIR) or Finite Impulse Response (FIR) techniques.

Artifacts that are predominant in the low frequency range (e.g.: 0-4 Hz) are preferably removed so as to improve detection accuracy at a later stage.

Each sub-band signal $X_i(t)$ is preferably spatially filtered using a Common Spatial Patterns (CSP) filter. The CSP filter can be trained by joint maximization/minimization of the variances for two classes of EEG involved. A spatially filtered signal for $i^{th}$ band, $Y_i(t)$, can be obtained:

$$Y_i(t) = WX_i(t)$$

where W is a CSP projection matrix. The rows of W are the stationary spatial filters and the columns of $W^{-1}$ are the common spatial patterns. The spatially filtered signal $Y_i(t)$ maximizes the differences in the variance of the two classes of EEG measurements. However, the variances of only a small number m of the spatially filtered signal $Y_i(t)$ are preferably used as features for classification. The m first and last rows of $Y_i(t)$ preferentially form a CSP feature vector $O_i^t$:

$$O_i^t = \log\left(\text{var}(Y_i(t)) / \sum_{i=1}^{2m} \text{var}(Y_i(t))\right)$$

where $$\text{var}(Y_i(t)) = \sum_{\tau=t_1}^{t=t_1+t_2} (Y_i(t+\tau) - \overline{Y}_i)^T (Y_i(t+\tau) - \overline{Y}_i)$$

and where $t_1$, and $t_2$, are the starting and ending time of a moving window, and $(\bullet)^T$ denotes the transpose of the matrix $(\bullet)$.

A concatenated feature vector $O^t$ for classification is preferably formed by concatenating all CSP feature vectors $O_i^t$ from the sub-bands as follows:

$$O^t = [O_1^t, O_2^t K, O_N^t]$$

During a calibration session in an example embodiment, the user 102 is asked to perform tasks with and without motor intent. The concatenated feature vector $O^t$ is advantageously fed to a model of motor intent, F, which is built from data collected during the calibration session. The output of the model motor intent, F, is a continuous score $S_a^t$ indicative of the degree of motor intent:

$$S_a^t = F(O^t, \Lambda_a)$$

where $\Lambda_a$ denotes the model parameters for motor intent detection.

A probabilistic model $P_r(S_a^t)$ from the continuous motor intent score $S_a^t$ is obtained in the example embodiment by fitting it with a Gaussian distribution:

$$P_r(S_a^t) = \frac{1}{(2\pi\sigma^2)^{1/2}} \exp\left\{\frac{1}{2\sigma^2}(S_a^t - \mu)^2\right\}$$

Figure 2:
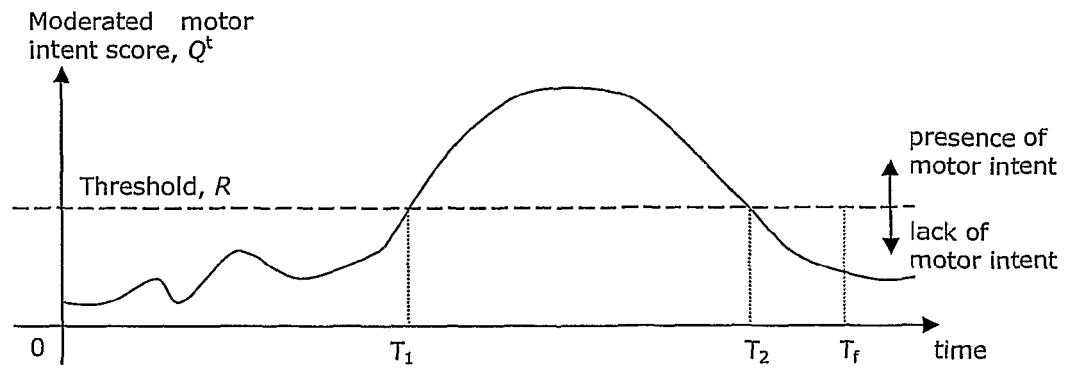
FIG. 2 is a graph illustrating example values of a moderated motor intent score $Q^r$ over a period of time, according to an example embodiment of the present invention.

The probabilistic model $P_r(S_a^t)$ is moderated to belong to a fixed range between 0 and 100:

$$Q^t = \frac{100}{1 + \exp\{-\beta P_r(S_a^t)\}}$$

where $Q^t$ is a moderated motor intent score and $\beta$ is a positive constant. FIG. 2 is a graph illustrating example values of the moderated motor intent score $Q^t$ over a period of time. The values are preferably asynchronously and continuously detected over the period of time.

A moderated threshold value R can be set such that any value of $Q^t$ below R can be interpreted as a lack of motor intent, resulting in a failure to elicit motor assistance from the robotic device. Conversely, any value of $Q^t$ above R can be interpreted as a presence of motor intent.

An effective score $\lambda(t)$ is obtained with the example embodiment by rectifying the difference between the moderated motor intent score $Q^t$ and the moderated threshold value R:

$$\lambda(t) = \begin{cases} Q^t - R, & \text{if } (Q^t - R) > 0 \\ 0, & \text{if } (Q^t - R) \leq 0 \end{cases} \quad (1)$$

The effective score may be mapped to D, an extent of assistive movement provided by the robotic device. The mapping D may be realized by a linear scaling of the integral of $\lambda(t)$:

$$D = c\int_0^{T_f} \lambda(t) dt \quad (2)$$

where c is a positive scaling constant, and $$T_f = \underset{t>T_1}{\arg\min}\{|Q^t(t) - \alpha R|\}$$

$T_f$ is the trial duration and can be defined as the time taken for the moderated score $Q^t$ to first return to a pre-specified fraction a of the moderated threshold value R (for example, see FIG. 2). α is a constant, ranging from $0<\alpha<1$, that can be adjusted from a configuration file. The distance moved by the user's 102 limb with assistance from the robot preferably provides feedback to the user 102 on the degree of his/her motor intent.

Robotic assistance provided by the robotic device 118 to the user 102 can be advantageously adapted by autonomously adjusting the moderated threshold value R based on a user-specific learning curve that takes into account past measures of the user's 102 movement performance. A performance index $P_k$, is evaluated for a kth session, $k=1,2,\ldots,n$, consisting of $N_k$ trials, as $$P_k = \frac{1}{N_k} \sum_{i=1}^{N_k} D_i$$

A desired performance index P* can be established by taking into account the distance between a target position (for example, position 120b in FIG. 1) and a starting position (for example, position 120a in FIG. 1). A relative performance index ΔP with respect to the target may be obtained:

$$\Delta P = P_k - P^* \quad (3)$$

A positive value of ΔP indicates a performance surplus while a negative value of ΔP indicates a performance deficit. When a current session shows a performance surplus, the moderated threshold value R may be increased in a subsequent session so as to motivate the user 102 to further improve his/her motor output in an effortful manner. Conversely, when there is a performance deficit in the current session, the moderated threshold value R may be decreased in the subsequent session to avoid frustrating the user 102. As motor skill improves, additional task demands may be introduced so as to continually motivate the user 102 to be cognitively involved when undertaking tasks encountered during the session, thereby engaging mechanisms of learning that drive the reorganization of damaged pathways and maps in the user's 102 brain. A fine balance is advantageously struck between a rehabilitation program that is under-stimulating and one that is exceedingly difficult to the extent of creating undue stress for the user 102.

A variation in threshold value $\Delta R$ may be defined by:

$$\Delta R = R_{k+1} - R_0 \quad (4)$$

where $R_0$ is a default threshold value. After obtaining the relative performance index $\Delta P$ at the end of the kth session, a corresponding value of $\Delta R$ can be inferred from a learning curve f: $\Delta P \rightarrow \Delta R$. Then, the moderated threshold value for the (k+1)th session is obtained as $R_{k+1} = \Delta R + R_0$.

Figure 3:
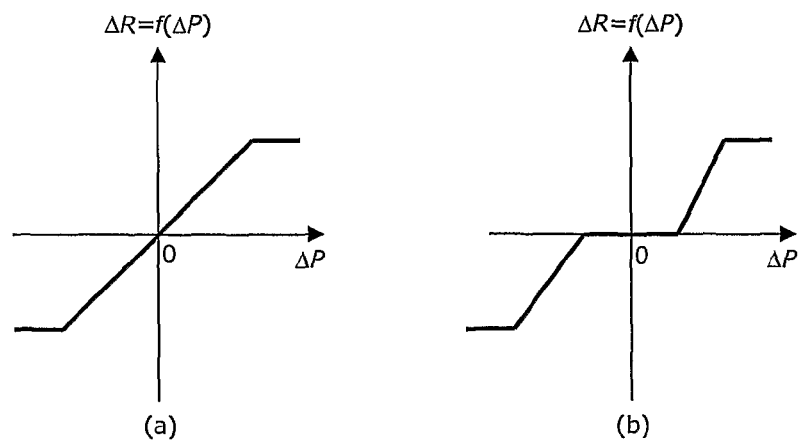
FIG. 3(a) is an example of a default learning curve according to an example embodiment of the present invention.
FIG. 3(b) is an example of an alternative learning curve according to an example embodiment of the present invention.

FIG. 3(a) is an example of a default learning curve according to an example embodiment of the present invention. FIG. 3(b) is an example of an alternative learning curve according to an example embodiment of the present invention, comprising a dead zone. The learning curve is preferentially stored as a lookup table for inference in future sessions. In order to limit the variation in threshold value $\Delta R$ to an acceptable range, the learning curve is preferably saturated when $\Delta P$ exceeds a certain value (see FIG. 3(a) or (b)). It will be appreciated by a person skilled in the art that for simplicity of representation, the learning curves shown in FIGS. 3(a) and (b) are piecewise linear functions. However, nonlinear functions may also be used to model the learning curves.

Figure 4:
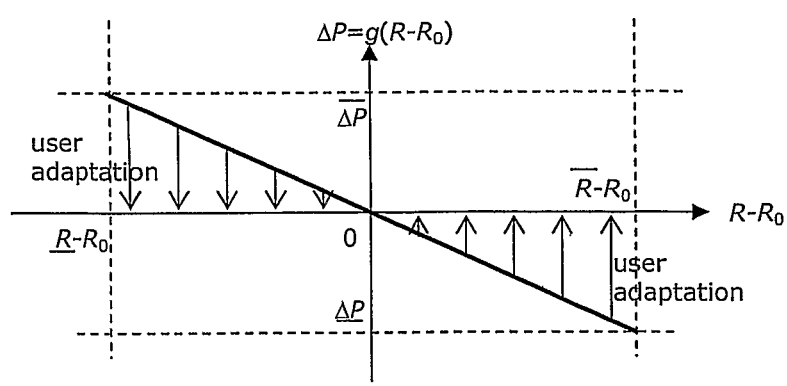
FIG. 4 is a graph illustrating an example of a performance curve, according to an example embodiment of the present invention.

The learning curves can be user specific and autonomously generated depending on the performance of the user 102 in the previous session. The default threshold value $R_0$ may be obtained from a calibration session:

$$R_0 = \underset{\underline{R} < R < \overline{R}}{\operatorname{argmin}} |P_0 - P^*| \quad (5)$$

where $$P_0 = \frac{1}{N_0} \sum_{i=1}^{N_0} D_i$$

is the default performance, computed as a mean value over $N_0$ trials in the calibration session, and $\underline{R}, \overline{R}$ are bounds in the search space of R. Note that $P_0$ depends on the threshold R, since $D_i$ defined in (2), depends on R through (1). In other words, the default threshold $R_0$ is the value of R that yields the closest match between the default performance $P_0$ and the desired performance $P^*$. Before calibration, $P^*$ is a default value from a configuration file. After calibration, when $R_0$ is obtained, $P^*$ is set to the value of $P_0$ corresponding to $R_0$, i.e. $P^* := P_0|_{R=R_0}$. Then, a map g:$(R-R_0) \rightarrow \Delta P$ can be obtained by varying the moderated threshold value R within a neighborhood of $R_0$, i.e. $R \in [\underline{R}, \overline{R}]$, and computing $\Delta P$ from (3) corresponding to each value of R. An example of the map g:$(R-R_0) \rightarrow \Delta P$, which is hereinafter referred to as a performance curve, is illustrated conceptually in FIG. 4. In order to smoothen the performance curve, a least squares approximation or other techniques may be used. Again, it will be appreciated by a person skilled in the art that for simplicity of representation and without a loss of generality, the performance curve shown in FIG. 4 is a linear function.

When the moderated threshold value R is increased, it can become more difficult to elicit robotic assistance for a given degree of motor intent. To attain a same level of performance, i.e. drive the limb to the target location (for example, position 120b in FIG. 1), the user 102 preferably increases his/her motor intent above the new increased moderated threshold value R in the subsequent sessions.

Conversely, when the moderated threshold value R is decreased, it can become easier to elicit robotic assistance, and the user 102 tends to decrease the surplus of motor intent in the subsequent sessions to conserve effort. As such, it may be assumed that $\Delta P \rightarrow 0$ after a sufficient number of sessions during which the user 102 adapts to the fixed threshold. With this assumption, the learning curve f is obtained from the performance curve g by the expression:

$$f(\Delta P) = \begin{cases} -g^{-1}(\Delta P), & \text{for } \underline{\Delta P} < \Delta P < \overline{\Delta P} \\ -g^{-1}(\overline{\Delta P}), & \text{for } \Delta P \geq \overline{\Delta P} \\ -g^{-1}(\underline{\Delta P}), & \text{for } \Delta P \leq \underline{\Delta P} \end{cases} \quad (6)$$

When the relative performance index $\Delta P$ is within the limits $\underline{\Delta P} < \Delta P < \overline{\Delta P}$, the learning curve f is advantageously a negative inversion of the performance curve g (for example, see FIG. 4), so as to preferentially obtain $\Delta P = 0$. When the relative performance is outside the limits $\underline{\Delta P} < \Delta P < \overline{\Delta P}$, saturation is imposed. This preferably yields a default learning curve of which an example is shown in FIG. 3(a).

For better flexibility in catering to the needs of different users 102, alternative learning curves can be advantageously set and its associated parameters manually selected. To reduce the sensitivity of threshold change when the performance is near the desired level, a dead zone in the learning curve can be advantageously implemented, where $$f(\Delta P) = 0 \text{ for } \underline{\Delta P} < \underline{dz} \leq \Delta P \leq \overline{dz} < \overline{\Delta P} \quad (7)$$

of which an example of the alternative learning curve is shown in FIG. 3(b). This dead zone advantageously has the effect of enhancing the stability of adaptation.

The user-specific performance curve may be autonomously computed by varying the moderated threshold value R within a neighborhood of the default threshold value $R_0$. Thereafter, the learning curve $\Delta R = f(\Delta P)$ may be generated. The performance curve preferably provides an estimate of how the user's 102 performance changes in response to a change of the threshold, and is only computed during calibration.

The user-specific learning curve advantageously quantifies the change of the moderated threshold value R needed for a subsequent motor learning session based on the performance curve and the performance measures of a current session. In other words, the moderated threshold value $R_{k+1}$ for the (k+1)th session is preferably computed based on the default threshold value $R_0$ and the performance index $P_k$ in the kth session, for k=1,2, . . . n. Additional calibration sessions may be periodically conducted after n sessions to update the learning curve. The learning curve can be derived from the assumption that the user 102 adapts his/her mental effort to keep the motor performance constant.

Data comprising an extent of assistive movement D that may be provided to the user 102 is preferentially sent from the computer system 110 to the robot control module 114 via cable 112. It will be appreciated that in different embodiment, a wireless connection may be used. The robot control module 114 preferably utilizes the data to control the robotic device 118 such that the robotic device 118 can advantageously administer forces to provide motor assistance to the user 102. In addition, the robotic device 118 can sense and record movement trajectories and forces. For example, the distance moved by the user's 102 limb with assistance from the robotic device 118 may provide feedback to the user 102 on the degree of his/her motor intent.

The extent of assistive movement D is advantageously sent as a desired set point in a task space. For smooth human-like movement, a minimum jerk desired trajectory $x_d(t)$ may be computed:

$$x_d(t) = D\left(6\left(\frac{t}{T}\right)^5 - 15\left(\frac{t}{T}\right)^4 + 10\left(\frac{t}{T}\right)^3\right) \quad (8)$$

where T is the time to complete the movement, specified in the configuration file. With the minimum jerk desired trajectory $x_d(t)$ established, an impedance controller (not shown) may then be used to drive the user's 102 limb (which can be coupled to the robotic device 118 as illustrated in FIG. 1) along the desired trajectory. The impedance control can provide safe and compliant motion of the robotic device 118 by controlling the mechanical interaction with the user's 102 limb.

Figure 5:
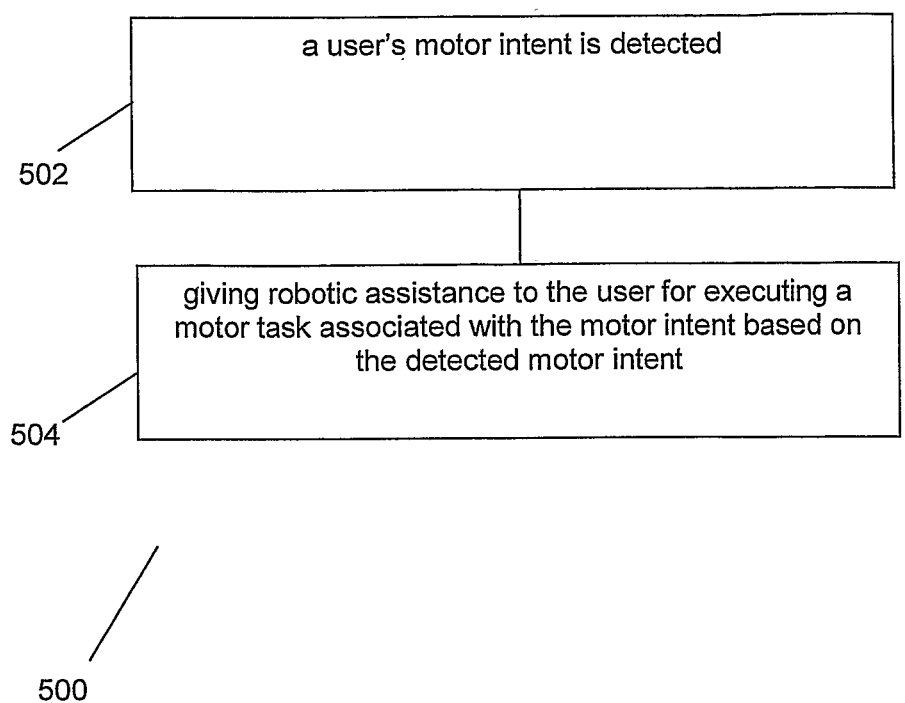
FIG. 5 is a flow chart illustrating the steps of a method for motor learning with an adaptive brain-robot interface, according to an example embodiment of the present invention.

FIG. 5 is a flow chart illustrating the steps of a method for motor learning with an adaptive brain-robot interface, according to an example embodiment of the present invention. At step 502, a user's motor intent is detected. At step 504, a robotic assistance is given to the user for executing a motor task associated with the motor intent based on the detected motor intent.

Figure 6:
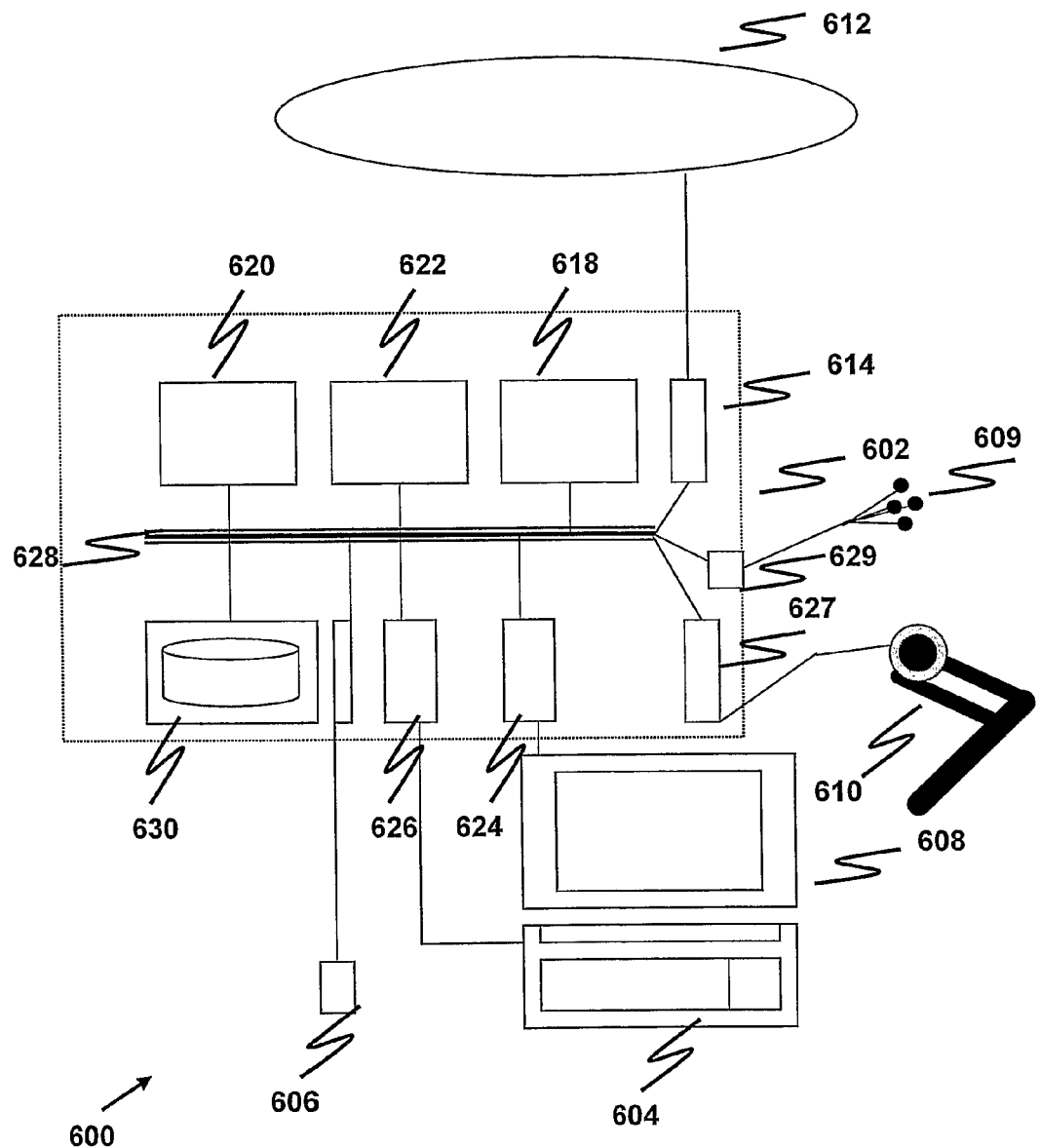
FIG. 6 is a schematic of a computer system for implementing the system and method for motor learning in example embodiments.

The method and system of the example embodiment can be implemented on the computer system 600, schematically shown in FIG. 6. It may be implemented as software, such as a computer program being executed within the computer system 600, and instructing the computer system 600 to conduct the method of the example embodiment.

The computer system 600 comprises a computer module 602, input modules such as a keyboard 604 and mouse 606 and a plurality of output devices such as a display 608, detector 609 and robotic device 610.

The computer module 602 is connected to a computer network 612 via a suitable transceiver device 614, to enable access to e.g. the Internet or other network systems such as Local Area Network (LAN) or Wide Area Network (WAN).

The computer module 602 in the example includes a processor 618, a Random Access Memory (RAM) 620 and a Read Only Memory (ROM) 622. The computer module 602 also includes a number of Input/Output (I/O) interfaces, for example I/O interface 624 to the display 608, I/O interface 626 to the keyboard 604, I/O interface 627 to the robotic device 610, and I/O interface 629 to the detector 609.

The components of the computer module 602 typically communicate via an interconnected bus 628 and in a manner known to the person skilled in the relevant art.

The application program is typically supplied to the user of the computer system 600 encoded on a data storage medium such as a CD-ROM or flash memory carrier and read utilizing a corresponding data storage medium drive of a data storage device 630. The application program is read and controlled in its execution by the processor 618. Intermediate storage of program data maybe accomplished using RAM 620.

Embodiments of the present invention advantageously detect, in an asynchronous manner, a continuous measure of movement intent from the neural signals acquired non-invasively from the user, and use the measure to control the extent of movement assisted by the robotic device. Performance and effort measures may be used to generate autonomously a user-specific learning curve, which governs the adaptation of robotic assistance provided to the user.

Detection in an asynchronous manner in addition advantageously does not require the user to time his/her motor imagery and mental effort relative to a cue in order to control the robotic device.

Automatic adaptation of robotic assistance based on past performance and the learning curve advantageously means that when there is a performance surplus, the threshold is increased, leading to an increased difficulty in activating robotic assistance. On the other hand, in the presence of a performance deficit, the threshold is decreased for greater ease in activating robotic assistance.

By taking into account cognitive processes that play key roles in motor learning, embodiments of the present invention provide a system and method for motor learning that can potentially enlarge the group of user s who can benefit from motor learning.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

The invention claimed is:

1. A method of motor learning comprising the steps of:
providing a brain-robot interface and a robotic device, the brain-robot interface comprising a neural signal acquisition device;
detecting a user's motor intent using the neural signal acquisition device;
using a processing unit:
obtaining a first score based on the detected motor intent; and
calculating a second score based on the first score and a threshold score value for the motor intent, including adjusting the threshold score value for the motor intent by extracting a value from an obtained learning curve that maps a relative performance index to a relative target threshold value variation to quantify an amount of threshold score value adjustment; and
using the robotic device to give robotic assistance to the user for executing a motor task associated with the motor intent based on the second score.

2. The method as claimed in claim 1, wherein obtaining the first score comprises processing signals detected by the neural signal acquisition device to derive the first score associated with the detected motor intent.

3. The method as claimed in claim 1, wherein adjusting the threshold score value comprises comparing a target performance in relation to the motor task with an actual performance, and lowering the threshold score value if there is a deficit of the actual performance compared to the target performance, and increasing the threshold score value if there is a surplus in the actual performance compared to the target performance.

4. The method as claimed in claim 3, wherein the target performance and the actual performance are compared over a session, k, of $N_k$ trials, and the threshold score value is adjusted for a next session, k+1, based on the session k.

5. The method as claimed in claim 3, further comprising obtaining a default threshold score value, $R_0$, for a first session, k=1, from a calibration process.

6. The method as claimed in claim 5, wherein the default threshold score value is obtained as a value that yields a closest match between the target performance and the actual performance in a calibration process.

7. The method as claimed claim 1, wherein the detecting of the user's motor intent is performed asynchronously.

8. The method as claimed in claim 1, wherein the detecting of the user's motor intent is performed substantially continuously.

9. The method as claimed in claim 1, wherein obtaining the learning curve comprises computing the relative performance index corresponding to values of the threshold score value within a neighborhood of a default threshold score value.

10. A system for motor learning comprising:
   a brain-robot interface comprising a neural signal acquisition device for detecting a user's motor intent;
   a processing unit for obtaining a first score based on the detected motor intent, and for calculating a second score based on the first score and a threshold score value for the motor intent, the processing unit being configured for adjusting a threshold score value for the motor intent by extracting a value from a learning curve that maps a relative performance index to a relative target threshold value variation to quantify an amount of threshold score value adjustment; and
   a robotic device for giving robotic assistance to the user for executing a motor task associated with the motor intent;
   wherein the robotic device is configured for giving of the robotic assistance based on the second score.

11. The system as claimed in claim 10, wherein the processing unit is configured for processing signals detected by the neural signal acquisition device to derive the first score associated with the detected motor intent.

12. The system as claimed in claim 10, wherein the processing unit is configured for lowering the threshold score value if there is a deficit of an actual performance compared to a target performance, and for increasing the threshold score value for giving the robotic assistance if there is a surplus in the actual performance compared to the target performance.

13. The system as claimed in claim 12, wherein the processing unit is configured for comparing the target performance and the actual performance over a session, k, of $N_k$ trials, and the threshold is adjusted for a next session, k+1, based on the session k.

14. The system as claimed in claim 12, wherein the processing unit is further configured for obtaining a default threshold, $R_0$, for a first session, k=1, from a calibration process.

15. The system as claimed in claim 14, wherein the processing unit is further configured for obtaining the default threshold score value as a value that yields a closest match between the target performance and the actual performance in a calibration process.

16. The system as claimed in claim 10, wherein the detector is configured for detecting of the user's motor intent asynchronously.

17. The system as claimed in claim 10, wherein the detector is configured for detecting of the user's motor intent substantially continuously.

18. The system as claimed in claim 10, wherein the processing unit is configured for obtaining the learning curve by computing the relative performance index corresponding to values of the threshold score value within a neighborhood of a default threshold score value.

* * * * *